United States Patent
Von Roeschlaub et al.

(10) Patent No.: US 6,866,514 B2
(45) Date of Patent: Mar. 15, 2005

(54) GEL ELECTROPHORESIS TRAINING AID AND TRAINING KIT

(75) Inventors: Priscilla Von Roeschlaub, Port Washington, NY (US); Rachel C. Von Roeschlaub, Port Washington, NY (US)

(73) Assignee: Von Enterprises, Inc., Port Washington, NY (US)

( * ) Notice: Subject to any disclaimer, the term of this patent is extended or adjusted under 35 U.S.C. 154(b) by 0 days.

(21) Appl. No.: 10/356,267

(22) Filed: Jan. 31, 2003

(65) Prior Publication Data

US 2004/0152059 A1 Aug. 5, 2004

(51) Int. Cl.[7] .......................... G09B 23/00; G09B 23/26
(52) U.S. Cl. .................. 434/295; 434/262; 434/276; 434/280; 434/296; 434/279
(58) Field of Search ................. 434/276–297; 435/309.4

(56) References Cited

U.S. PATENT DOCUMENTS 4,438,300 A * 3/1984 Morse ................. 379/447
2004/0085716 A1 * 5/2004 Uke

* cited by examiner

*Primary Examiner*—Derris H. Banks
*Assistant Examiner*—Dmitry Suhol
(74) *Attorney, Agent, or Firm*—Pitney Hardin LLP

(57) ABSTRACT

A gel electrophoresis training aid is provided. The training aid includes a substantially transparent elastomeric body having at least one series of spaced-apart wells. The elastomeric body is adapted with a plurality of spaced-apart bands extending in the same direction from the wells. Each of the spaced-apart bands are positioned substantially parallel to one spaced-apart well. A training kit including the training aid is also provided.

17 Claims, 4 Drawing Sheets

GEL ELECTROPHORESIS TRAINING AID AND TRAINING KIT

FIELD OF THE INVENTION

The present invention relates to a training aid for teaching individuals gel electrophoresis and more particularly to an elastomeric body adapted for loading with a simulated biomolecule containing solution.

BACKGROUND OF THE INVENTION

Gel electrophoresis is a standard tool of molecular biologists and biochemists in their continuing study of biomolecules. The ability to separate biomolecules (e.g., DNA, RNA and protein) by molecular weight or electronic charge has resulted in numerous advances in medicine. As a result of the widespread usage of gel electrophoresis, secondary schools (e.g., High Schools) are now incorporating the theory and process of gel electrophoresis into their respective curriculums. In fact, some states are now requiring the theory and application of gel electrophoresis to be part of the school curriculum.

Although gel electrophoresis has become standard analytical tool, hands-on training of individuals (such as on the secondary education level) is not feasible due in part to the prohibitive costs associated with the gel electrophoresis equipment. The preparation and use of actual gels is also laborious which does not facilitate widespread training. Pre-made gels are another option. However, costs for pre-made gels can be prohibitive. Available gel electrophoresis kits that use agarose gels are fragile, expensive and can only be used once. Thus, conventional gels are not suitable for the widespread instruction of individuals.

According, there is a need in the art for training aids to instruct individuals on gel electrophoresis while avoiding the time consuming preparation and costs associated with the use of actual gels. Accordingly, it is an object of the present invention to provide a reusable, training aid that is relatively simple and inexpensive to manufacture to facilitate widespread training of individuals.

SUMMARY OF THE INVENTION

The present invention provides a gel electrophoresis training aid that is durable and reusable particularly suited for training individuals the theory and applications of gel electrophoresis. The training aid includes a substantially transparent elastomeric body with at least one series of spaced-apart wells. The spaced-apart wells preferably extend along a single axis. The elastomeric body is adapted with a plurality of spaced-apart bands extending in the same direction from the wells, in which each spaced-apart band is positioned substantially parallel to one spaced-apart well. In one preferred embodiment, one or more wells have a plurality of spaced-apart bands positioned substantially parallel to each well. The bands are of any color with the color blue being preferred. Likewise, the wells and bands have substantially the same surface area. In another embodiment, the elastomeric body includes two series of spaced-apart wells. Preferably, the elastomeric body is a substantially planar body. The elastomeric body is preferably made from a thermoset or thermoplastic resin. One preferred resin is a silicone-based material.

The elastomeric body of the training aid is preferably adapted with a substantially transparent polymeric sheet having a plurality of spaced-apart bands. In one embodiment, the polymeric sheet is disposed in the elastomeric body. In another embodiment, the polymeric sheet is disposed on the elastomeric body.

A gel electrophoresis training kit is also provided. The kit includes at least one training aid of the invention and at least one instruction pamphlet providing written directions for using the training aid. The training kit also preferably includes a container including a liquid simulating a biomolecule-containing solution for filling the wells. The training kit also preferably includes at least one filling device for filling the wells of the elastomeric body the liquid. In one embodiment, the liquid is colored with blue being preferred.

DETAILED DESCRIPTION OF THE INVENTION

The present invention provides a simple and unique training aid for instructing individuals on gel electrophoresis. Instruction kits containing the training aid of the invention are also provided.

Figure 1:
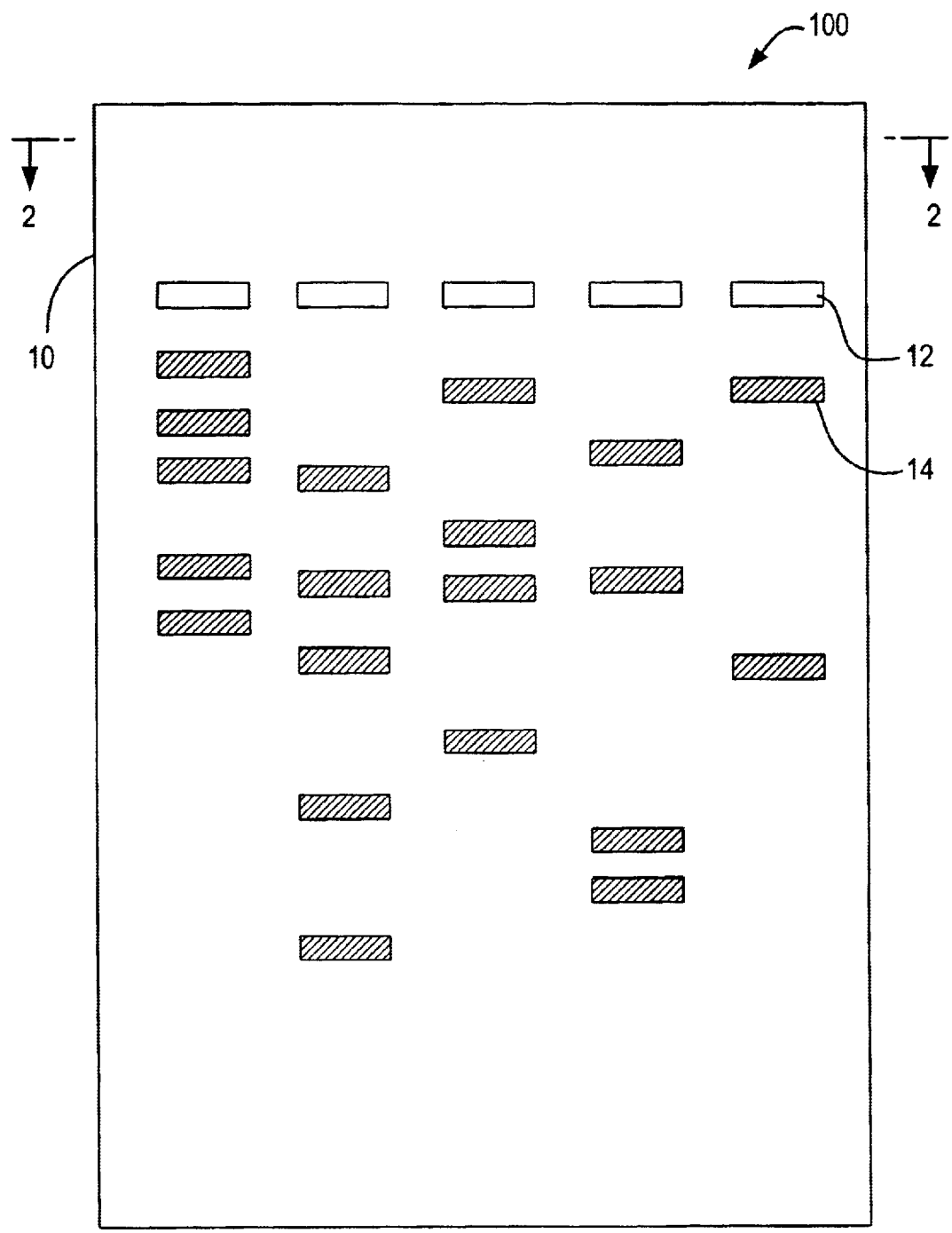
FIG. 1 is a plan view of one embodiment of the training aid of the present invention having a single row of spaced-apart wells for loading.

Referring to FIG. 1, a plan view of one embodiment of the gel electrophoresis training aid is shown. Same numbered reference numerals in various views refer to elements of the invention common to those views. Training aid 100 includes a substantially transparent elastomeric body 10 provided with at least one series of spaced-apart wells 12, preferably extending along a single axis (i.e., extends as a single row). Reference to "substantially transparent" in this context means that the elastomeric material is not opaque. In a more preferred embodiment, the elastomeric body is transparent. The elastomeric body can also be colored or colorless depending on the desired aesthetics of the training aid. Elastomeric body 10 is preferably in the form of a slab, with polygonal geometries such as rectangle or square being more preferred, to provide a realistic simulation of an electrophoresis gel. Wells 12 are spaced-apart at predetermined intervals to allow for simulated loading of the wells with a simulated biomolecule containing solution as described further below. Reference to a "well" in this context means a cavity or indentation disposed in and partially extending through elastomeric body 10. Wells 12 simulate loading wells found in conventional electrophoresis gels and thus will contain a liquid when filled.

In accordance with the invention, elastomeric body 10 is adapted with a plurality of spaced-apart colored bands 14 extending in the same direction from wells 12. Bands 14 simulate biomolecule bands (i.e., DNA, RNA or protein separated by molecular weight or electronic charge through the use of gel electrophoresis). To provide a more realistic simulation of a conventional gel, each of the spaced-apart bands 14 are positioned substantially parallel to one spaced-apart well 12. Moreover, as will be apparent to those skilled in the art, one or more wells 12 disposed in elastomeric body 10 may omit bands 14 extending there from. In one preferred embodiment, bands 14 are the color blue. Likewise, in alternative embodiments of the invention, different patterns of bands 14 are used to simulate the different sequences of biomolecules being separated.

Figure 2:
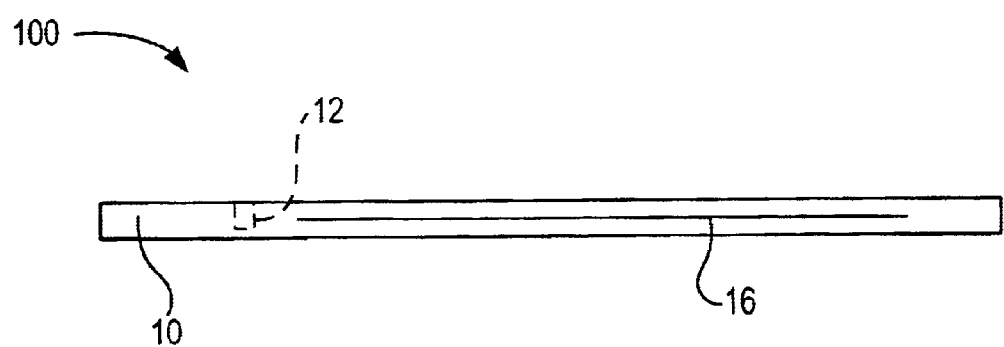
FIG. 2 is a cross-sectional view of the training aid depicted in FIG. 1 taken along line 2—2.

As shown in FIG. 2, elastomeric body 10 is adapted with bands 14 by disposing a transparent polymeric sheet 16 in elastomeric body 10. Sheet 16 is transparent except for portions provided with simulated bands 14. Sheet 16 is provided with bands 14 using any technique known in the art. For example, bands 14 can be printed on sheet 16 using a laser or inkjet printer. Other techniques can also be easily used.

Elastomeric body 10 is prepared using any technique known in the art for preparing elastomeric materials. In one preferred embodiment, elastomeric body 10 is molded from any thermoset or thermoplastic elastomer. In another preferred embodiment, a two-part elastomer resin/activator system is used thereby providing a cross-linked or vulcanized material. The system can be moisture-curable, heat-curable or free-radical initiated. One preferred elastomeric resin to be used is a silicone (i.e., siloxane-based) resin. An example of a commercially available two-part silicone/activator system is the P-44 system sold by Silicones, Inc, in High Point, N.C. Another example of a commercially available system is the Silflex resin with like hardener sold by United Resins in Royal Oak, Mich. In another embodiment, elastomeric body 10 is formed by injection molding a thermoplastic elastomer.

As will be apparent to one skilled in the art viewing FIG. 2, sheet 16 is disposed in elastomeric body 10 by first partially pouring the activated elastomeric resin in the mold, positioning sheet 16 on the poured material and thereafter pouring the remainder of the activated elastomeric resin. Alternatively, elastomeric body 10 is first molded and sheet 16 is laminated to one of the exterior surfaces of elastomeric body 10 with a suitable (e.g., water-resistant or water-proof) adhesive. Preferably, the adhesive is colorless. An example of an adhesive to be used is an acrylate- or methacrylate-based epoxy. Sheet 16 can be laminated to the surface disposed with wells 12 or to the opposite surface (i.e., the surface of elastomeric body 10 omitting wells 12). The lamination of sheet 16 is particularly advantageous when elastomeric body 10 is formed using injection molding.

Figure 3:
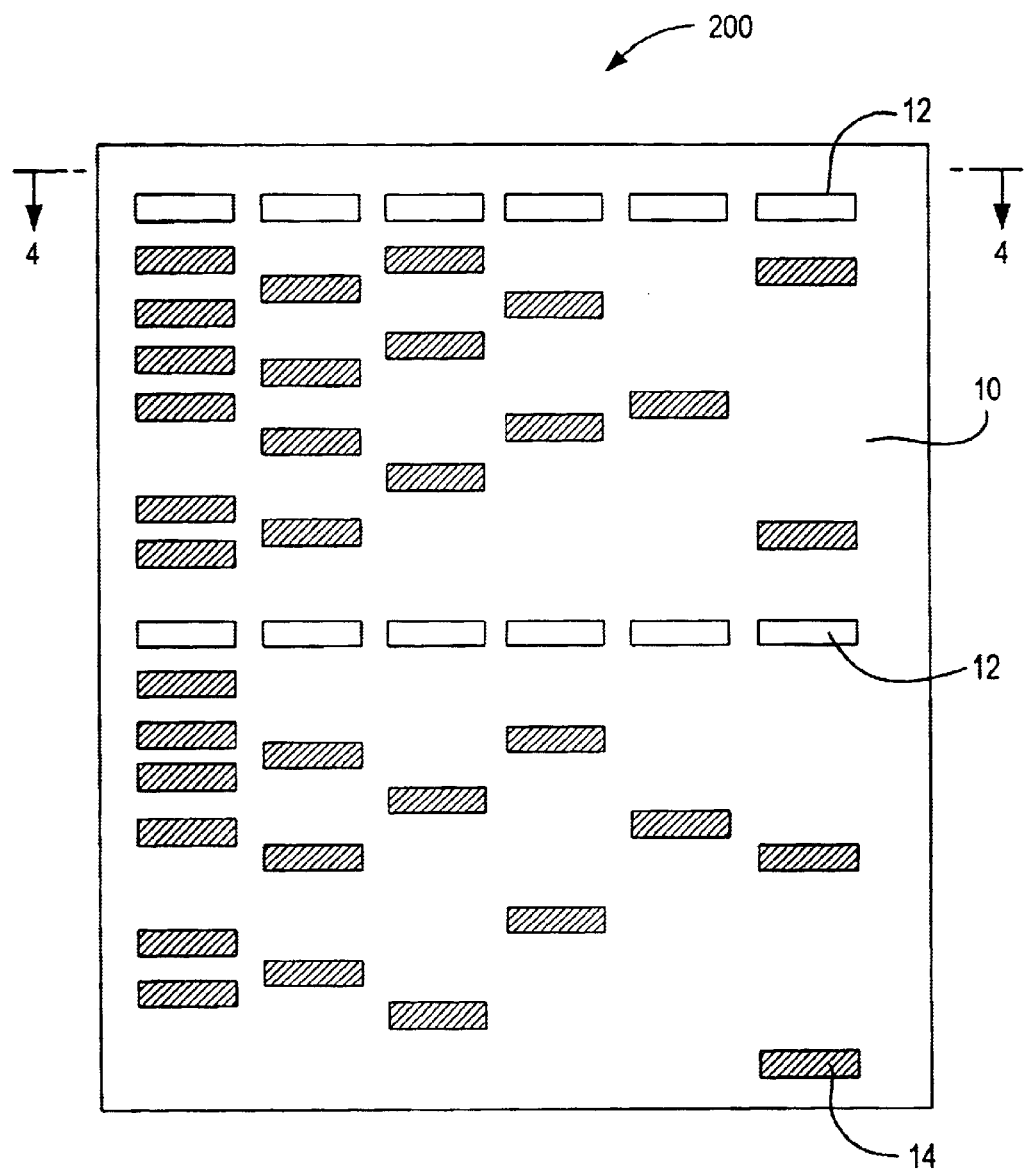
FIG. 3 is a plan view of another embodiment of the training aid of the present invention having a double row of spaced-apart wells for loading.
Figure 4:
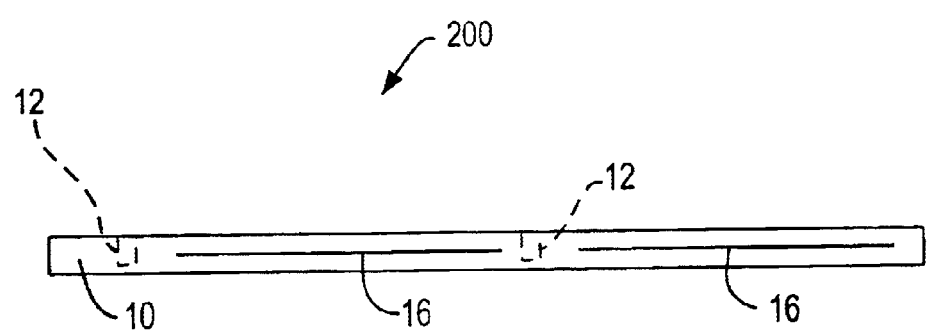
FIG. 4 is a cross-sectional view of the training aid depicted in FIG. 3 taken along line 4—4.

FIG. 3 shows a plan view of an alternative embodiment of the training aid of the invention. Training aid 200 includes an elastomeric body 10 provided with two parallel series of spaced-apart wells 12, each preferably extending along single axis. Preferably, as shown in FIG. 3, one of the series of wells 12 is disposed proximal to one edge of elastomeric body 10 with the second series of wells 12 being disposed intermediate two opposing edges of elastomeric body 10. Each series of wells 12 are spaced-apart at predetermined intervals to allow for simulated loading of the wells. In manner analogous to training aid 100, elastomeric body 10 is adapted with a plurality of spaced-apart colored bands 14 extending in the same direction from each series of wells 12. Each of the spaced-apart bands 14 is positioned substantially parallel to one spaced-apart well 12. Moreover, as described above, one or more wells 12 disposed in elastomeric body 10 may not have any bands 14 extending there from. In one preferred embodiment, bands 14 are the color blue. A cross-sectional view of training aid 200 is depicted in FIG. 4. In this embodiment, as with FIG. 3, elastomeric body 10 is adapted with bands 14 by disposing two (2) transparent polymeric sheets 16 in elastomeric body 10. Sheet 16 is transparent except for portions provided with simulated bands 14. Alternatively, a single sheet 16 with both sets of band 14 is laminated to either of the exterior surfaces of elastomeric body 10 using an adhesive. Elastomeric body 10 is formed as described above.

The present invention also provides a training kit including the training aid of the invention. The kit preferably includes at least one training aid and at least one instruction pamphlet having written matter providing instructions on using the training aid of the invention to simulate loading electrophoresis gels. In a more preferred embodiment, the kit includes at least one container with simulated biomolecule-containing solution. The solution is preferably colored (e.g., blue) and non-toxic. An example of a suitable solution is water (or a water-based solution) containing a blue food dye. The kit also preferably includes at least one filling device for loading wells 12. Examples of filling devices to be used include, but are not limited to, pipettes, micropipettes, and eyedroppers.

The training aid of the invention is used by an individual to provide a hands-on learning experience where preparation and use of an actual gel is not feasible. The training aid of the present invention is used to simulate real world applications and to review fundamental genetic engineering techniques; including gene splicing, DNA sequencing, gene location and forensic DNA matching (DNA fingerprinting). Individuals using the training aid can examine the patterns of bands 14 (simulating DNA, RNA or protein), analyze the migration distances between bands 14 and learn how to determine the size of unknown biomolecule fragments. In accordance with the invention, wells 12 are used for loading practice. Individuals can pipette different volumes of liquid sample into wells 12 to practice the eye-hand coordination needed for loading real gels. Once instruction is completed the training aid can be washed (e.g., with water) and dried for later re-use.

EXAMPLE

A training aid was prepared in the following manner. The gel electrophoresis mold was thoroughly cleaned with an air compressor to remove all dust and debris. The mold was a custom mold made by Creative Models, Inc., (Hicksville, N.Y.). In a clean, two-gallon plastic bucket 650 grams of silicone resin (product number P44A) and 65 grams of hardener (product number P44B) were combined to provide a 10:1 parts by weight mixture. The silicone/hardener mixture was thoroughly blended by hand for 5 minutes using a metal spatula. The silicon/hardener mixture was placed in a vacuum and degassed for ten minutes at 30 lbs to remove any entrained air.

The degassed silicone/hardener mixture was poured into the training aid mold until it was approximately half full. The poured mixture was allowed to harden for about 1 hour. An acetate plastic strip with printed, simulated DNA bands was placed on top of the hardening mixture so that the bands and lanes (i.e., wells) were in line with each other (i.e., substantially parallel). The remainder of the mixture was then poured on top of the acetate plastic strip to seal it inside the hardening resin. The mold was allowed to stand for 24 hours to complete hardening. Once the resin hardened to form the elastomeric body, the training aid was removed from the mold by gently pulling the training aid loose from the mold. Any excess silicone was trimmed from the edges of the training aid.

We claim:
1. A gel electrophoresis training aid comprising:
    a substantially transparent elastomeric body including at least one series of spaced-apart wells extending as a single row, each of said wells partially extending through said elastomeric body and being adapted for loading with a liquid, said elastomeric body being adapted with a plurality of spaced-apart, colored bands to simulate separated biomolecules, wherein said bands extend in a substantially same columnar direction from said wells, and wherein each band is positioned to run substantially parallel in said columnar direction to only one well.

2. The training aid of claim 1, wherein one or more wells have a plurality of spaced-apart, colored bands positioned to run substantially parallel to said well.

3. The training aid of claim 1, wherein said elastomeric body includes two series of spaced-apart wells, each series extending as a single row.

4. The training aid of claim 1, wherein said elastomeric body is substantially planar body.

5. The training aid of claim 3, wherein said elastomeric body is adapted with a substantially transparent polymeric sheet having said plurality of spaced-apart, colored bands.

6. The training aid of claim 5, wherein said polymeric sheet is disposed in said elastomeric body.

7. The training aid of claim 5, wherein said polymeric sheet is disposed on said elastomeric body.

8. The training aid of claim 7, wherein said polymeric sheet is laminated to said elastomeric body.

9. The training aid of claim 8, wherein said polymeric sheet is laminated to said elastomeric body on a side opposite from said spaced-apart wells.

10. The training aid of claim 1, wherein said elastomeric body is of a thermoset or thermoplastic resin.

11. The training aid of claim 1, wherein each of said spaced-apart wells and each of said spaced-apart, colored bands have substantially the same surface area.

12. The training aid of claim 1, wherein said spaced-apart, colored bands are of a blue color.

13. A gel electrophoresis training kit comprising:

at least one training aid being a substantially transparent elastomeric body including at least one series of spaced-apart wells extending as a single row, each of said wells partially extending through said elastomeric body and being adapted for loading with a liquid and said elastomeric body being adapted with a plurality of spaced-apart, colored bands to simulate separated biomolecules, wherein said bands extend in a substantially same columnar direction from said wells, and wherein each band is positioned to run substantially columnar only one well; and at least one instruction pamphlet providing written directions for using said training aid.

14. The training kit of claim 13, further comprising a container including a liquid simulating a biomolecule-containing solution for filling said wells.

15. The training kit of claim 14, further comprising at least filling device for filling said wells of said elastomeric body with said liquid.

16. The training kit of claim 14, wherein said liquid is colored.

17. The training kit of claim 16, wherein liquid is colored blue.

* * * * *